US007416839B2

(12) United States Patent
Bergmann et al.

(10) Patent No.: US 7,416,839 B2

(45) Date of Patent: Aug. 26, 2008

(54) "PRIONINS", HIGHLY SPECIFIC MARKERS FOR NONINVASIVE PRESYMPTOMATIC DETECTION OF TSE DISEASES, AND TARGETS FOR THERAPEUTIC REAGENTS TO PREVENT AND CONTROL TSE DISEASES IN ANIMALS AND HUMANS

(75) Inventors: Johanna Bergmann, Hamburg (DE); Enrique Preddie, Montreal (CA)

(73) Assignee: Altegen, Inc., Wilmington, DE (US)

( * ) Notice: Subject to any disclaimer, the term of this patent is extended or adjusted under 35 U.S.C. 154(b) by 649 days.

(21) Appl. No.: 10/386,921

(22) Filed: Mar. 12, 2003

(65) Prior Publication Data

US 2006/0147908 A1 Jul. 6, 2006

(51) Int. Cl.
*G01N 33/53* (2006.01)

(52) U.S. Cl. .......................... 435/5; 435/7.1; 435/7.94; 435/962; 435/970

(58) Field of Classification Search ...................... None
See application file for complete search history.

(56) References Cited

FOREIGN PATENT DOCUMENTS

| | | |
|---|---|---|
| EP | 125 023 | 4/1984 |
| EP | 171 496 | 3/1985 |
| EP | 173 494 | 8/1985 |
| EP | 184 187 | 12/1985 |
| WO | 86/01533 | 3/1986 |
| WO | 87/02671 | 5/1987 |

OTHER PUBLICATIONS

Baranyi et al. (1995) "The antisense homology box: A new motif within proteins that encodes biologically active peptides" *Nature Medicine* 1:894-901.

Beidler et al. (1988) "Cloning and high level expression of a chimeric antibody with specificity for human carcinoembryonic antigen" *J. Immunol.* 141:4053-4060.

Bergmann et al. (1996) "'Alzas', a protein found in brain and blood of humans with Alzheimer's Disease (AD) but not in normal humans, appears to be the causative biochemical factor of all forms of AD" *Neurobiology of Aging* 17:S14.

Better et al. (1988) "*Escherichia coli* Secretion of an Active Chimeric Antibody Fragment" *Science* 240:1041-1043.

Blake et al. (1984) "A Rapid, Sensitive Method for Detection of Alkaline Phosphatase-Conjugated Anti-antibody on Western Blots" *Anal. Biochem.* 136:175-179.

Bontems et al. (1991) "Refined Structure of Charybdotoxin: Common Motifs in Scorpion Toxins and Insect Defensins" *Science* 254:1521-1523.

Collinge et al. (1996) "Molecular Analysis of Prion Strain Variation and the Aetiology of 'New Variant' CJD" *Nature* 283:685-690.

Darcel (1995) "Reflections on Scrapie and Related Disorders, With Consideration of the Possibility of a Viral Aetiology" *Vet. Res Commun.* 19:231-252.

Dluzewski et al. (1989) "Red Cell Membrane Protein Distribution During Malarial Invasion", *J. cell Sci.* 92:691-699.

Goldfarb et al. (1965) "The Transmissible Spongiform Encephalorathies" *Annual Rev. Med.* 46:57-65.

Harrison (1996) "Peptide-surface Association: The case of PDZ and PTB Domains" *Cell* 86:343-344.

Hill et al. (1991) "Crystal Structure of Defensin HNP-3, an Amphiphilic Dimer: Mechanisms of Membrane Permeabilization" *Science* 251:1481-1485.

Hopp et al (1981) "Prediction of Protein Antigenic Determinants From Amino Acid Sequences" *Proc. Natl. Acad. Sci. USA* 78:3824-3828.

Jones et al. (1986) "Replacing the Complementarity—Determining Regions in a Human Antibody With Those From a Mouse" *Nature* 321:552-525.

Kaneko et al. (1998) Evidence for Protein X binding to a Discontinuous Epitope on the Cellular Prion Protein During Scrapie Prion Propagation *Proc. natl. Acad. Sci. USA* 94:10069-10074.

Kimberlin et al. (1989) "The Role of the Spleen in the Neuroinvasion of Scrapie in Mice" *Virus Res.* 12:201-211.

Kozak (1984) "Compilation and Analysis of Sequences Upstream From the Translational Start Site in Eukaryotic mRNAs" *Nucleic Acid Res.* 12:857-872.

Lasmezas et al. (1997) "Transmission of the BSE Agent to Mice in the Absence of Detectable Abnormal Prion Protein" *Science* 275:402-405.

Liu et al. (1987) "Production of a Mouse-Human Chimeric Monoclonal Antibody to CD20 With Potent Fc-Dependent Biologic Activity" *Proc. Natl. Acad. Sci. USA* 84:3439-3443.

Liu et al. (1987) "Chimeric Mouse-Human IgG1 Antibody That Can Mediate Lysis of Cancer Cells" *J. Immunol.* 139:3521-3526.

Mestel (1996) "Putting Prions to the Test" *Science* 273:184-189.

Morrison (1985) "Transfectomas Provide Novel Chimeric Antibodies" *Science* 229:1202-1207.

Nishimura et al. (1987) "Recombinant Human-Mouse Chimeric Monoclonal Antibody Specific for Common Acute Lymphocytic Leukemia Antigen" *Canc. Res.* 47:999-1005.

Oi et al. (1986) "Chimeric Antibodies" *BioTechniques* 4:214.

Peitsch et al. (1990) "Localization and Molecular Modelling of the Membrane-Inserted Domain of the Ninth Component of Human Complement and Perforin" *Mol. Immunol.* 27 589-602.

Prusiner (1991) "Molecular Biology of Prion Diseases" *Science* 252:1515-1522.

(Continued)

*Primary Examiner*—Bruce Campell
*Assistant Examiner*—Michelle Horning
(74) *Attorney, Agent, or Firm*—Frommer lawrence & Haug LLP

(57) ABSTRACT

Proteins expressed from within the prion protein genes of all animals and humans, "prionins", against which reagents can be prepared for accurate pre-symptomatic diagnosis, for detecting latent TSE, for detecting TSE contamination of food, blood and blood products and for therapeutic treatment of Bovine spongiform encephalopathy (BSE) in cows, Scrapie disease in sheep and Creutzfeldt-Jacob syndrome in humans, are revealed.

7 Claims, 11 Drawing Sheets

OTHER PUBLICATIONS

Figure 3A:
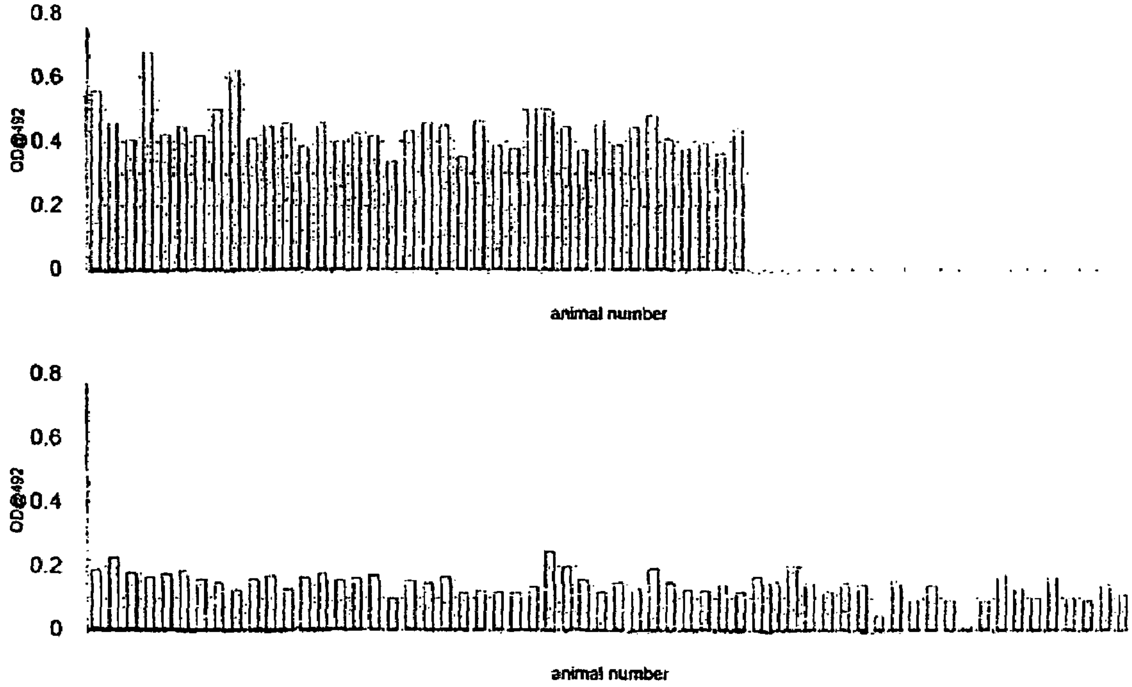

Prusiner (1996) "Transgenetics and Gene Targeting in Studies of Prion Diseases" *Current topics in Microbiology and Immunology* 207:95-123.

Schägger et al. (1987) "Tricine-Sodium Dodecyl Sulfate-Polyacrylamide Gel Electrophoresis for the Separation of Proteins in the Range From 1 to 100 kDa" *Anal. Biochem.* 166:368-379.

Scheuner et al. (1996) "Secreted Amyloid β-protein Similar to That in the Senile Plaques of Alzheimer's Disease is Increased in vivo by the Presenilin 1 and 2 and *APP* Mutations Linked to Familial Alzheimer's Disease" *Nature Medicine* 2:864-870.

Schmerling et al. (1998) "Expression of Amino-Terminally Truncated PrP in the Mouse Leading to Ataxia and Specific Cerebellar Lesions" *Cell* 93:203-214.

Schreuder et al. (1996) "Preclinical Test for Prion Diseases" *Nature* 381:563.

Shaw et al. (1988) "Mouse/Human Chimeric Antibodies to a Tumor-Associated Antigen: Biologic Activity of the Four Human IgG Subclasses" *J. Natl. Cancer Inst.* 80:1553-1559.

Sun et al. (1987) "Chimeric Antibody with Human Constant Regions and Mouse Variable Regions Directed Against Carcinoma-Associated Antigen 17-1A" *Proc. Natl. Acad. Sci. USA* 84:214-218.

Telling (1995) "Prion Propagation in Mice Expressing Human Chimeric PrP Transgenes Implicates the Interaction of Cellular PrP with Another Protein" *Cell* 83:79-90.

van Leeuwen et al. (1998) "Frameshift Mutants of β Amyloid Precursor Protein and Ubiquitin-B in Alzheimer's and Down Patients" *Science* 279:242-247.

Verhoeyan et al. (1988) "Reshaping Human Antibodies: Grafting an Antilysozyme Activity" *Science* 239:1534.

Westaway et al. (1995) "On Safari with PrP: Prion Diseases of Animals" *Trends. Microbiol.* 3:141-147.

Wills et al. (1989) "Induced Frameshifting Mechanism of Replication for an Information-Carrying Scrapie Prion" *Microbiol. pathogenesis* 6:235-249.

Wood et al. (1985) "The Synthesis and in vivo Assembly of Functional Antibodies in Yeast" *Nature* 214:446-449.

Yolken (1982) "Enzyme Immunoassays for the Detection of Infectious Antigens in Body Fluids: Current Limitations and Future Prospects" *Rev. Infect. Dis.* 4:35.

Zhou et al. (1996) "Structural Basis for IL-4 Receptor Phosphopeptide Recognition by the IRS-1 PTB Domain" *Nature Struct. Biol.* 3:388-393.

FIG 1 a

MEHWGEPIPRTGQSWRQPLSTSGRGWLG
SAPSRWLGPASWRWLGPASWRWLGSAPW
WWLGTATWWRLGSRWYPRSMEQTQ b

MEHWGEPIPGTGQSWRQPLPTSGRGWLGS
APWRWLGPTSWRWLGSAPWWLGTATWWW
RLGSRW c

MEHWGQPIPGAGQPWRQPLPTSGRWWLGA
ASWWWLGAASWWWLGAAPWWWLGSRRWHP
QSVEQAE d

MGAAGDNLMVVVGVSPMAVDGAKEGVPII
SGTSPANQKPTSSIWQGLRQLGQ e

MGTAPWWWLGTTSWWWLGSAPWWWLGSRR
WHPQSVEQAQ

FIG 2

| | |
|---|---|
| BSAS | **RLGSRWYPRSMEEQTQ** |
| SCRAPAS | **PLPTSGRGWLGSAPWR** |
| CJAS | **GSRRWHPQSVEQAE** |
| HAMPAS | **RRWHPQSVEQAQ** |
| MPAS | **SPMVDGAKEGVP** |

upper = positive
lower = negative upper = positive
lower = negative

Figure 4

| | |
|---|---|
| | 48 69 |
| BSAS | **WRWLGSAPWWWLGTATWWWRLG** |
| | 40 61 |
| SCRAPAS | **WRWLGSAPWWWLGTATWWWRLG** |
| CJAS | 25 52 |
| | **WWLGAASWWWLGAASWWWLGAAPWWWLG** |

(a)
Figure 5
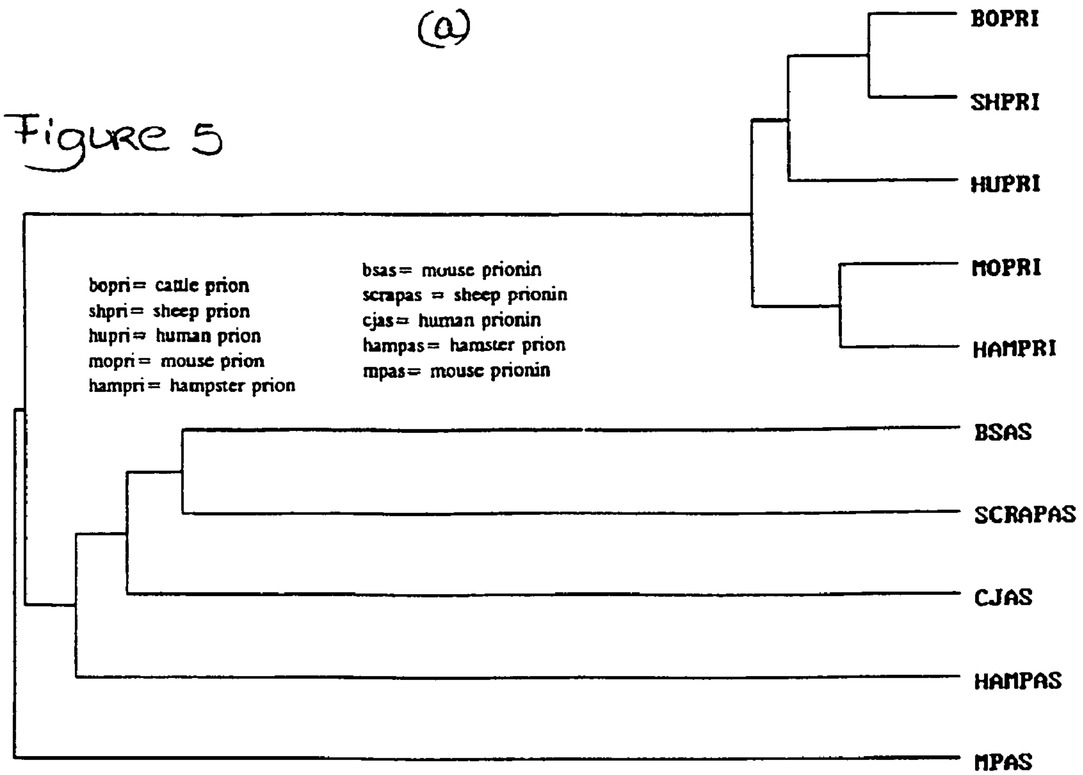
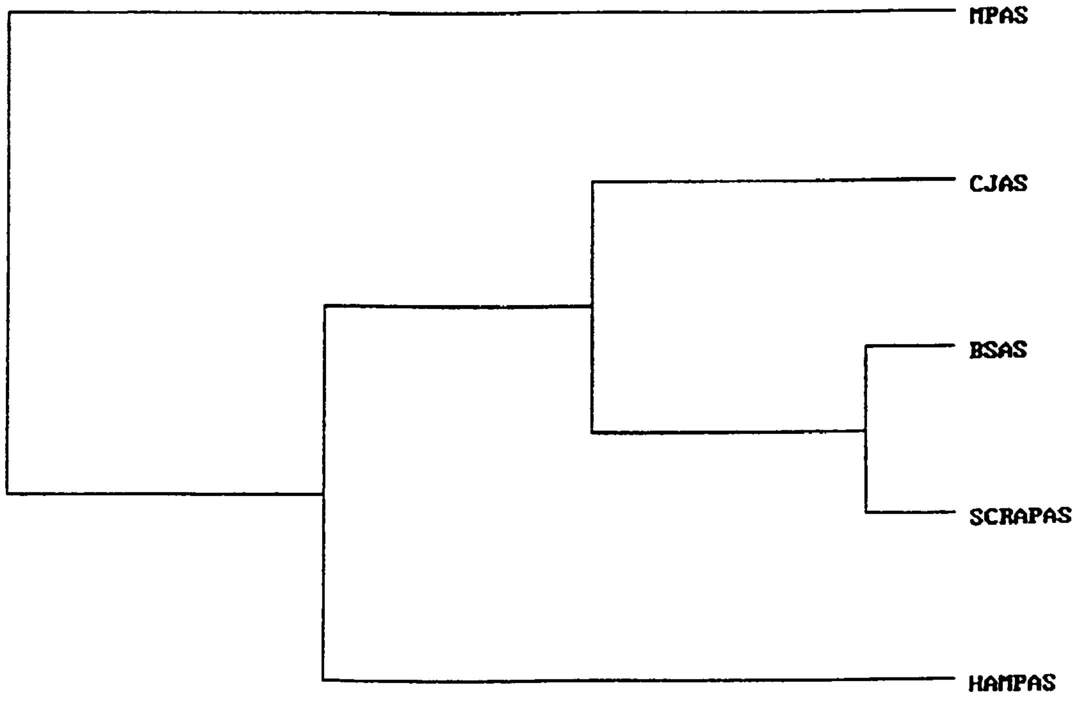

SEQUENCE LISTING

```
<160> NUMBER OF SEQ ID NOS: 13

<210> SEQ ID NO 1
<211> LENGTH: 81
<212> TYPE: PRT
<213> ORGANISM: bovine

<400> SEQUENCE: 1

Met Glu His Trp Gly Glu Pro Ile Pro Arg Thr Gly Gln Ser Trp Arg
1               5                   10                  15

Gln Pro Leu Ser Thr Ser Gly Arg Gly Trp Leu Gly Ser Ala Pro Ser
            20                  25                  30

Arg Trp Leu Gly Pro Ala Ser Trp Arg Trp Leu Gly Pro Ala Ser Trp
        35                  40                  45

Arg Trp Leu Gly Ser Ala Pro Trp Trp Trp Leu Gly Thr Ala Thr Trp
    50                  55                  60

Trp Trp Arg Leu Gly Ser Arg Trp Tyr Pro Arg Ser Met Glu Gln Thr
65                  70                  75                  80

Gln
```

-continued

<210> SEQ ID NO 2
<211> LENGTH: 64
<212> TYPE: PRT
<213> ORGANISM: sheep

<400> SEQUENCE: 2

```
Met Glu His Trp Gly Glu Pro Ile Pro Gly Thr Gly Gln Ser Trp Arg
1               5                   10                  15

Gln Pro Leu Pro Thr Ser Gly Arg Gly Trp Leu Gly Ser Ala Pro Trp
            20                  25                  30

Arg Trp Leu Gly Pro Thr Ser Trp Arg Trp Leu Gly Ser Ala Pro Trp
        35                  40                  45

Trp Trp Leu Gly Thr Ala Thr Trp Trp Trp Arg Leu Gly Ser Arg Trp
    50                  55                  60
```

<210> SEQ ID NO 3
<211> LENGTH: 65
<212> TYPE: PRT
<213> ORGANISM: homo sapiens

<400> SEQUENCE: 3

```
Met Glu His Trp Gly Gln Pro Ile Pro Gly Ala Gly Gln Pro Trp Arg
1               5                   10                  15

Gln Pro Leu Pro Thr Ser Gly Arg Trp Trp Leu Gly Ala Ala Ser Trp
            20                  25                  30

Trp Trp Leu Gly Ala Ala Ser Trp Trp Trp Leu Gly Ala Ala Pro Trp
        35                  40                  45

Trp Trp Leu Gly Ser Arg Arg Trp His Pro Gln Ser Val Glu Gln Ala
    50                  55                  60

Glu
65
```

<210> SEQ ID NO 4
<211> LENGTH: 52
<212> TYPE: PRT
<213> ORGANISM: mouse

<400> SEQUENCE: 4

```
Met Gly Ala Ala Gly Asp Asn Leu Met Val Val Val Gly Val Ser Pro
1               5                   10                  15

Met Ala Val Asp Gly Ala Lys Glu Gly Val Pro Ile Ile Ser Gly Thr
            20                  25                  30

Ser Pro Ala Asn Gln Lys Pro Thr Ser Ser Ile Trp Gln Gly Leu Arg
        35                  40                  45

Gln Leu Gly Gln
    50
```

<210> SEQ ID NO 5
<211> LENGTH: 39
<212> TYPE: PRT
<213> ORGANISM: hamster

<400> SEQUENCE: 5

```
Met Gly Thr Ala Pro Trp Trp Trp Leu Gly Thr Thr Ser Trp Trp Trp
1               5                   10                  15

Leu Gly Ser Ala Pro Trp Trp Trp Leu Gly Ser Arg Arg Trp His Pro
            20                  25                  30

Gln Ser Val Glu Gln Ala Gln
```

-continued

35

<210> SEQ ID NO 6
<211> LENGTH: 16
<212> TYPE: PRT
<213> ORGANISM: bovine
<220> FEATURE:
<221> NAME/KEY: UNSURE
<222> LOCATION: (1)..(16)
<223> OTHER INFORMATION: Sequence of antigenic epitopes

<400> SEQUENCE: 6

Arg Leu Gly Ser Arg Trp Tyr Pro Arg Ser Met Glu Glu Gln Thr Gln
1 5 10 15

<210> SEQ ID NO 7
<211> LENGTH: 16
<212> TYPE: PRT
<213> ORGANISM: sheep

<400> SEQUENCE: 7

Pro Leu Pro Thr Ser Gly Arg Gly Trp Leu Gly Ser Ala Pro Trp Arg
1 5 10 15

<210> SEQ ID NO 8
<211> LENGTH: 14
<212> TYPE: PRT
<213> ORGANISM: Homo sapiens

<400> SEQUENCE: 8

Gly Ser Arg Arg Trp His Pro Gln Ser Val Glu Gln Ala Glu
1 5 10

<210> SEQ ID NO 9
<211> LENGTH: 12
<212> TYPE: PRT
<213> ORGANISM: mouse

<400> SEQUENCE: 9

Arg Arg Trp His Pro Gln Ser Val Glu Gln Ala Gln
1 5 10

<210> SEQ ID NO 10
<211> LENGTH: 12
<212> TYPE: PRT
<213> ORGANISM: hamster

<400> SEQUENCE: 10

Ser Pro Met Val Asp Gly Ala Lys Glu Gly Val Pro
1 5 10

<210> SEQ ID NO 11
<211> LENGTH: 22
<212> TYPE: PRT
<213> ORGANISM: bovine
<220> FEATURE:
<221> NAME/KEY: DNA_BIND
<222> LOCATION: (1)..(22)
<223> OTHER INFORMATION: sequence of DNA positive regulator of BSAS
from 48 to 69 in the c omplete sequence ( See SEQ ID NO: 1

<400> SEQUENCE: 11

Trp Arg Trp Leu Gly Ser Ala Pro Trp Trp Trp Leu Gly Thr Ala Thr
1 5 10 15

Trp Trp Trp Arg Leu Gly
20

-continued

```
<210> SEQ ID NO 12
<211> LENGTH: 22
<212> TYPE: PRT
<213> ORGANISM: sheep
<220> FEATURE:
<221> NAME/KEY: DNA_BIND
<222> LOCATION: (1)..(22)
<223> OTHER INFORMATION: sequence of DNA positive regulator of SCRAPAS
      from 40 to 61 in the complete sequence (SEE SEQ ID NO: 2

<400> SEQUENCE: 12

Trp Arg Trp Leu Gly Ser Ala Pro Trp Trp Trp Leu Gly Thr Ala Thr
1               5                   10                  15

Trp Trp Trp Arg Leu Gly
            20


<210> SEQ ID NO 13
<211> LENGTH: 28
<212> TYPE: PRT
<213> ORGANISM: homo sapiens
<220> FEATURE:
<221> NAME/KEY: TRANSMEM
<222> LOCATION: (1)..(28)
<223> OTHER INFORMATION: membrane spanning helix of CJAS from amino
      acid 25 to amino acid 52 in the complete sequenc

<400> SEQUENCE: 13

Trp Trp Leu Gly Ala Ala Ser Trp Trp Trp Leu Gly Ala Ala Ser Trp
1               5                   10                  15

Trp Trp Leu Gly Ala Ala Pro Trp Trp Trp Leu Gly
            20                  25
```

"PRIONINS", HIGHLY SPECIFIC MARKERS FOR NONINVASIVE PRESYMPTOMATIC DETECTION OF TSE DISEASES, AND TARGETS FOR THERAPEUTIC REAGENTS TO PREVENT AND CONTROL TSE DISEASES IN ANIMALS AND HUMANS

CROSS-REFERENCE TO RELATED APPLICATIONS

This application claims the benefit of and priority to PCT Applications PCT/EP98/03609 filed Jun. 16, 1998 and CA 2,206,774 filed Jun. 16, 1997.

STATEMENT REGARDING FEDERALLY SPONSORED RESEARCH AND DEVELOPMENT

Not applicable.

FIELD OF THE INVENTION

This invention is related to diagnostic and therapeutic molecules for the detection, prevention of bovine spongiform encephalopathy (BSE), scrapie disease (scrapie) and Creutzfeldt-Jakob syndrome (CJS). Specifically, the invention relates to three closely related proteins BSAS, SCRAPAS and CJAS which are implicated in causing BSE, scrapie and CJS, to antagonists of these proteins, to diagnostic reagents to detect these proteins in clinical samples and food, and to therapeutic methods directed at these proteins in animals and humans. It is also related to the use of homologues of these proteins from hamsters and mice which are useful for developing and testing methods for use with vaccines and other agents for therapeutic value in treatment of humans and animals for TSE diseases.

BACKGROUND OF THE INVENTION

Prion proteins (PrPs) are a family of very closely related proteins which are found in a number of allelic forms in the membrane of certain populations of brain neurons of all animals. PrPs are expressed in lymphoreticular system and replicated in spleen and other lymphoreticular tissues (Kimberin R. H. and Walker C. A. Virus Res. 12:201-211 (1989). The alteration of the molecular configuration (folding) of a PrP by an unknown mechanism which converts these proteins into infectious particles "prions" (PrPsc) is associated with a group of diseases called "Transmissible spongiform encephalopathies" (TSE) (Prusiner S. B. Science 252:1515-1522 (1991); Prusiner S. B. Ed., Current topics in Microbiology and Immunology 207 (1996)); (Westaway D et al., Trends. Microbiol. 3:141-147 (1995)); (Goldfarb L. G. and Brown P. Annu. Rev: Med. 46:57-65 (1965)).

Three members of the TSE family are of great economic and medical concern; these include Bovine spongiform encephalopathy (BSE) in cows, scrapie in sheep and Creutzfeldt-Jakob syndrome (CJS) in humans. Pathology of TSE involves nerve cell dysfunction, which leads to fatal neurodegeneration; TSEs are characterised by symmetrical vacuolation of neurons and neuropil and accumulation of PrPSc around neurons. The latter phenomenon is believed to be the cause of the phenotype of the disease in the affected animal or human (Darcel C. Vet. Res Commun. 19:231-252 (1995)).

Prions are believed to be self-replicating proteins, which in their altered configuration are resistant to destruction by proteolytic enzymes and heating conditions which usually, destroy most proteins. The infectious prion is believed to be transmissible across species. Nevertheless, it has not been satisfactorily explained how a brain resident protein which, so far has not been demonstrated in biological fluids, can be transmitted from animal to animal within a grazing herd of cattle. Also, it is a puzzle that an endogenous protein autoconverts from a harmless, useful, form to a highly pathogenic infective form; many exotic hypotheses have been proposed to explain these phenomena.

However a few plausible hypotheses have provided insight into some aspects of the above mentioned puzzle, e.g., (i) it has been shown that PrPsc can be detected in the tonsils of animals with BSE and scrapie and presumably, animals presymptomatic for the above diseases (Schreuder B. E et al., Nature 381:563 (1996); (ii) it has been suggested that prions could be receptors that ushers an unknown virus or other infectious agents into cells (Brown P. (quoted in special news report) "Putting Prions to the Test" Science 273:184-189 1996)); (iii) experiments in mice appear to indicate that PrP binds to a chaperon protein (protein X) which catalyses the formation of PrPSc (Telling G. C. Cell 83:79-90 (1995)); (iv) that an unidentified factor is responsible for BSE and prions act as host-adapting agent for the factor (Lasmezas C. I. et al Science 275:402-405 (1997), and (v) that a frame shift translation in scrapie PrP mRNA may play a role in conversion of PrP to PrPsc, (Wills P. R. et al. Microbiol. pathogenesis 6:235-249 (1989); Kiyotoshi K. et al.; Proc. natl. Acad. Sci. USA 94:10069-10074 (1998).

There is an intriguing relationship between Scrapie in sheep, BSE in cows and CJS in humans; it is believed that BSE is initiated by the scrapie prion and some forms of CJD are initiated by eating BSE infected cows, particularly brain. The latter appeared to be experimentally supported by the discovery, recently, of what has been called a BSE signature molecule in humans who contract a "new variant of CJD (Collinge, J et al., Nature 283:685-690 1996. Nevertheless despite a large international effort to understand the pathogenesis of TSE, and to develop non invasive widely applicable methods for presymptomatic detection of these diseases, which in the case of BSE and scrapie have calamitous effects on commercial activity and on the health of the population at large, substantial progress has not been made in these directions.

SUMMARY OF THE INVENTION

The object of the present invention was to find other proteins which were expressed in a disease-specific manner, and which might interact with and convert PrP to PrPsc. We reasoned that such proteins which would occur in body fluids, would be highly specific ante-mortem diagnostic markers in pre symptomatic cows, sheep and humans and they would be useful as therapeutic targets to manage the symptoms of TSE diseases in animals and humans. Furthermore, we aimed to invent a method/methods, which would detect cross infection of humans and other animals by such agents that cause BSE and scrapie.

According to the invention the solution to the problem was to use the implied relationship between human Alzheimer's disease (AD) and the prion diseases, especially the relationship of a protein ALZAS, which we have discovered to be the potential causative factor of all forms of AD. ALZAS (Bergmann J. E. et al., Neurobiology of Aging 17:S14 (1996), a protein encoded and expressed within the human APP gene; the latter is strongly linked to Alzheimer's disease (AD). The Post-translational modification of the APP gene product the "β amyloid precursor protein" is the β amyloid protein (Aβ).

Aβ plays a central role in the pathophysiology of AD (Scheuner D. et al., Nature Medicine 2:864-870 (1996)). Recently it was shown that protein products of frame shift mutations in the APP gene and the ubiquitin β gene might be involved in the pathology of Alzheimer's disease and Down syndrome (van Leeuwen F. et al., Science 279:242-247, (1998). ALZAS which is made up of Aβ, the APP protein transmembrane signal sequence and a unique intron encoded c-terminal sequence, is detected in brain, blood and saliva of all humans with Alzheimer's disease (AD), and has the predicted biochemical characteristics to initiate the clinical symptoms of AD (Bergmann J. E. et al., Neurobiology of Aging 17:S14 (1996)). The pathophysiological similarities between AD and the TSEs, particularly CJD, and the implied relationship of ALZAS to APP/Aβ led us to search for a molecule similar to ALZAS within the prion protein genes of cattle, sheep and humans, and in mice and hamsters. The two rodent species which have been used extensively by scientist wanting to model TSE diseases. Using the method which we call disease "gene discovery by positional searching" (DGDPS), (see Bergmann J. and Preddie E. "WIPO" publications No# WO98/07850 and No#WO98/07851). Our search led to the discovery of proteins BSAS, SCRAPAS and CJAS, which are encoded and expressed from within the PrP genes of cattle, sheep and humans respectively. Additionally we discovered MOPAS and HAMPAS, which were encoded within the PrP genes of mice and hamsters. Since these proteins were discovered within the chromosomal region encoding prion protein genes we named them "prionins". Following is a brief description of DGDPS as it was applied to the discovery of prionins Relationship of BSAS and SCRAPAS to BSE and Scrapie These proteins appear to be specifically related to the development of BSE in cattle and scrapie in sheep. BSAS and SCRAPAS appear in the blood of all animals with clinical symptoms of the disease and in a significant percentage of animals that have been exposed to the disease, but not usually in animals that have not been exposed to the disease. In addition, animals exposed to the disease produce specific antibody (endogenous antibody) directed against BSAS or SCRAPAS, which can be detected presymptomatic in the sera of affected animals. The concentration of the endogenous antibody in the serum of animals with clinical symptoms of the disease appears to be generally lower than that of the animals without clinical symptoms of the disease, which led us to speculate that there may be a weakening of a subjects immune defence at initiation of the disease.

BSAS and SCRAPAS

BSAS and SCRAPAS are relatively small β-sheet derived proteins expressed from within the prion protein genes of cows and sheep. These proteins are extremely hydrophobic, have the potential to bind strongly to the prion proteins and to convert them into the β-conformation. They also have sequence homologies to one region of the prion protein, which has been shown by others to be involved in the interaction of the so-called 'protein X' to the sheep prion protein. In addition to having the possibility of penetrating membranes, BSAS and SCRAPAS have structural similarities to powerful DNA-binding proteins and might autoactivate their own expression. They have about 60% overall similarity with each other. More than 20% of the amino acids are tryptophan as compared to the average tryptophan content <1% for all proteins for which the amino acid sequence is known.

Two epitopes (BSAS epi and SCRAPAS epi, 14 amino acids each) were selected, chemically synthesised and used to produce polyclonal antibodies against BSAS (BSAS pcAb) and SCRAPAS (SCRAPAS pcAb) in rabbits. Two subepitopes from within BSAS epi (BSAS mepi) and SCRAPAS epi (SCRAPAS mepi), were synthesised, amidated at the c-terminal end and used to affinity purify a specific population of antibodies from BSAS pcAb and SCRAPAS pcAb, respectively. These antibodies, and the mepi epitopes, were used in the ELISA tests which are described below.

ELISA Tests

Two types of ELISAs have been developed. One detects in serum the antigens BSAS respectively SCRAPAS, the other detects endogenous antibodies (specific IgG) against BSAS and SCRAPAS mepi epitopes. The specificity of all epitopes was confirmed both in commercial scale isolation of specific populations of IgG's from BSAS pcAb and SCRAPAS pcAb, and in the isolation of endogenous IgG from serum samples of selected BSE-infected cattle and scrapie-infected sheep. Potential cross-reacting antigenic epitopes were not found in the protein databases presently available.

Treatment of Serum Samples for Testing:

BSAS and SCRAPAS are extremely sensitive to freezing. Freezing overnight at −20° C. reduces the reaction of a positive sample by 70-80%; freezing at −80 ° C. eliminates the reaction completely. We believe that this high sensitivity to freezing is due to the high tryptophan content of the proteins, and the secondary structure enforced on the proteins by the tandem arrangements of several tryptophan triads in the proteins. The effect of freezing, although not as great for the Ab trap ELISA as for the Ag trap ELISA, seriously affects both ELISAs (antigen molecules with altered confirmation bind irreversible to endogenous IgG in positive sera which sometimes cause erratic ELISA results in the Ab trap assay). Therefore, frozen samples are not suitable for use in the ELISAs. Serum samples must be prepared from freshly drawn blood and stored at 4° C. for such investigations.

Outline of the Tests

The Antigen Trap Test

The wells of micro titre plates were coated with 100 μl of carbonate buffer, pH 9.6, containing 5 μg/ml mepi epitope-specific antibody, at 4° C. over night. The plates were washed 3× with ELISA washing buffer containing 0.05% Tween-20. Serum samples, 5 μl, were added to 45 μl of ELISA washing buffer containing 0.075% Tween-20, and incubated at 37° C. for 30 minutes. Wells were washed 5× with the 0.075% Tween-20 washing-buffer. 50 μl of second antibody (affinity purified SCRAPAS/BSAS-specific antibody, labelled with horseradish peroxidase (HRP)) diluted 1/40 in washing buffer containing 0.05% Tween-20, was added to each well and the plates were incubated at 37° C. for 45 minutes. The plates were again washed 5× with washing buffer containing 0.075% Tween-20. 50 μl substrate solution (Sigma OPD tablet set) was added to each well; colour development was allowed for 30 minutes in the dark, and the plates were read at 492 nm.

The Antibody Trap Test

The wells of micro titre plates were coated with 100 μl of carbonate buffer, pH 9.6, containing 10 μg/ml of each, BSAS mepi and SCRAPAS mepi epitopes, at 4° C. over night. The plates were washed 3× with ELISA washing buffer containing 0.05% Tween-20. Serum samples, 1.5μl, were added to 48.5μl of ELISA washing buffer containing 0.075% Tween-20, and incubated at 37° C. for 30 minutes. Wells were washed 5× with the 0.075 % Tween-20 washing buffer. 50 μl of second antibody (mixture of anti-bovine IgG and anti-sheep IgG antibodies (γ-chain specific, labelled with horse-radish peroxidase (HRP)) diluted 1/12000 in washing buffer containing 0.05% Tween-20, was added to each well and the plates were incubated at 37° C. for 45 minutes. The plates were again washed 5× with washing buffer containing 0.075% Tween-20. 50 μl substrate solution (Sigma OPD tablet set) was added to each well; colour development was allowed for 30 minutes in the dark, and the plates were read at 492 nm.

Description of DGDPS Procedure.

In general, first we identified a gene closely related to a gene already genetically or otherwise linked to a certain disease, then isolated the mRNA transcribed from the gene from disease tissue or patient's blood, then synthesised cDNA from the isolated mRNA with reverse transcriptase, then amplified the novel cDNA with specific primers which flanked the entire coding region of the cDNA, then we identified the cDNA from the size following electrophoresis on agarose gel, and finally isolated the unique cDNA from the agarose gel. This allowed us to select out the desired molecule, if it was expressed, without having to probe several million cDNA clones.

The procedure as used in the present invention and the results obtained are described in the following examples.

EXAMPLE 1

Discovery of Cattle PrP Prionin BSAS (1) We examined the sequenced regions within the bovine prion protein gene locus and selected potential complete orf's, i.e. with acceptable translation initiation sequences (see Kozak, M. Nucleic Acid Res. 12:857-872 (1984)) and translation termination stop codons (TAA, TAG or TGA) in place, (2) then, orf s fulfilling the above two characteristics were translated into putative protein sequences using the universal code, (3) then we analysed the putative protein with our proprietary computer assisted protein finger printing technology and obtained information about the potential biochemical characteristics of the deduced proteins, (4) next the biochemical characteristics of the deduced proteins were correlated with the known biochemical characteristics of BSE.

Then we determined if the protein was expressed: in order to do this two potential epitopes were identified/selected within the amino acid sequence at n-terminal and c-terminal of the deduced protein using the method of Hopp and Woods, K. R. Proc. Natl. Acad. Sci. USA 78:3824-3828 (1981). The sequences were compared to sequences in databases and those which appeared to have no homologue within the databases were selected. Mono-specific polyclonal rabbit antibodies were prepared against these and purified by immunoaffinity chromatography on CNBr-activated sepharose 4B (Pharmacia) according to a procedure which combined the first section of the recommendation of the manufacturer and the second section as described in Current Protocols in Molecular Biology (Vol 1) Ausubel, F. M. et al (ed) John Wiley & Sons NY. N.Y. 1991) and polyclonal IgG was coupled to horse radish peroxidase. An enzyme-based immunoassay format "sandwich ELISA" (described in "ELISA and other Solid Phase Immunoassays" (Kemeny, D. M. et al. (eds) John Wiley & sons, NY., N.Y. (1988), was used to probe serum, blood, saliva from BSE positive cows for BSAS using anti-BSAS IgG-HRP in a colorimetric reaction with "Sigma OPD" as substrate. The procedure is outlined in section above.

EXAMPLE 2

Detection of BSAS, SCRAPAS and CJAS in Clinical and Other Samples

Prionin proteins were detected using the ELISAs described above. Since some populations of the polyclonal anti-TSE antibodies cross react with domains of the major epitopes of each TSE species, with varying degrees of sensitivity, anti-SCRAPAS-HRP is used as the second antibody for detecting both BSAS and SCRAPAS, whereas either anti-SCRAPAS HRP or anti-CJAS-HRP is used as the second antibody for detecting CJAS.

EXAMPLE 3

Using another approach, which is not suitable for use as a routine test method (with BSAS as the example): BSAS protein was isolated from ~100 ul of serum, from an infected cow on a anti-BSAS antibody immuno-affinity column. The isolated protein was subjected to SDS gel electrophoresis as described by Schägger, H. and von Jabow, G. I. Anal. Biochem. 166:368-379 (1987) or by non-SDS PAGE. Following electrophoresis the proteins were subjected to Western blotting or spotted onto nylon membrane and treated with the affinity purified antibody. Interaction of the antibody with the protein bound to the membrane was visualised with a chemiluminescent kit purchased from Bio-Rad Inc. according to the manufacturer's instructions (also see Blake M. S. et al.Anal biochem. 136:175-179 (1984)). MOPAS and HAMPAS were discovered using the same procedure; however, the expression of these two proteins in animals with experimental TSE disease has not been investigated so far.

EXAMPLE 4

We have demonstrated, in the case of BSAS and SCRAPAS, a specific association (100%) of the proteins with animals confirmed with the disease or exposed in any manner to the disease; whereas the proteins were not associated with animals, which have never been exposed to the disease. BSAS and SCRAPAS was detected in serum of all animals clinically positive for the diseases and in the majority of animal that had no demonstrated clinical symptoms of the disease which came from herds that had even a single case of the disease. CJAS was detected in serum of two CJD victims in one of which was positive for both CJD and Alzheimer's disease.

DESCRIPTION OF THE PREFERRED EMBODIMENTS

The success of the present invention derived from our ability to find alternative genes encoding potentially pathogenic proteins BSAS, SCRAPAS and CJAS within the PrP genes of cattle, sheep and humans. The discovery of equivalent genes in mice and hamsters contributed to formulating our model for TSE.

DETAILS OF THE INVENTION

In detail the invention provides the following:

(i) Five protein molecules substantially free of natural contaminants, that encode a protein selected from BSAS, SCRAPAS, CJAS and MOPAS and HAMPAS. In particular the invention provides the aforementioned protein molecules wherein the sequence is SEQ ID NO: 1, SEQ ID NO: 2, SEQ ID NO: 3, SEQ ID NO: 4 and SEQ ID NO: 5.

(ii) A method for detecting latent CJD, BSE and scrapie in humans, cows and sheep respectively by using the ELISA method described above to detect endogenous IgG directed against an epitope in each protein BSAS (SEQ ID NO: 1); SCRAPAS (SEQ ID NO: 2) and CJAS (SEQ ID NO: 3) in blood of animals and humans respectively, that show no symptoms of the disease.

(iii) a method for detecting cross infection of animals by animals and human by animals by method described in (ii) above to detect the specific anti-prionin antibody in the blood of a subject.

(iii) A method of detecting contamination of meat, meat products and blood products by, BSAS (SEQ ID NO: 1), SCRAPAS (SEQ ID NO: 2) and CJAS (SEQ ID NO: 3), using one or both the ELISA methods described above to detect either the prionin or traces of a species specific anti prionin IgG in the product tested.

THE MOLECULES OF THE INVENTION

BSAS, SCRAPAS and CJAS ("prionins") are encoded and expressed from within bovine, sheep and human prion genes:

BSAS "SEQ ID NO: 1", is a 9.6 Kd basic protein containing 19.75% tryptophan (Trp) residues, a stretch of 22 amino acids (aa) which is a predicted positive DNA regulatory unit and which classifies the protein as a positive DNA regulator protein. The secondary structure of BSAS is organised as five (possibly seven) tandem, adjoining, β sheets each separated by a β turn. BSAS contains two regions of significant homology to regions of bovine prion protein between amino acids 90-150. The latter region has been suggested by others to be involved in the etiology of BSE in cows. It also has intriguing homology to growth hormone releasing hormone receptor.

SCRAPAS "SEQ ID NO: 2", is a 7.63 Kd basic protein. It contains 21.87% Trp residues and the identical predicted positive DNA regulatory domain, which is contained in BSAS. The secondary structure of SCRAPAS is organised as four or five equally spaced β sheets in a pattern almost identical to BSAS. It has no significant region of homology to the major sheep prion protein, but has moderate homology to the region (aa 90-150) described above in the bovine prion protein.

CJAS "SEQ ID NO: 3", is a 7.7 Kd basic protein. It contains 21.53% Trp residues. CJAS has a Pro-rich N-terminal region and a sequence of 27 amino acid, which contains a potential transmembrane helix, which classifies it as a transmembrane protein. The secondary structure of CJAS, which is similar to that of BSAS and SCRAPAS, is organised as four adjoining β pleats each separated by a β turn. The protein has a domain with significant homology to a domain in the malaria parasite merozoite membrane protein which is believed to promote vacuole formation which gives a spongiform appearance to infected erythrocytes (see Dluzewski A. R. et al J. cell Sci. 92:691-699 (1989)

MOPAS "SEQ ID NO: 4", is a 5.2 Kd neutral protein. It contains a single tryptophan residue (<0.5%). The secondary structure is organized as three equally separated β sheets separated by two broad alpha helical regions. It is not a β sheet structured protein.

HAMPAS "SEQ ID NO: 5", is a 4.79 Kd basic protein. It contains 26% tryptophan residues. It is basically a CJAS protein truncated at the N terminal. It shares an antigenic epitope with CJAS. The secondary structure is organised as three adjoining β pleats, which are arranged in a similar way to β-sheet 3,4 and 5 of CJAS.

BRIEF DESCRIPTION OF THE FIGURES AND TABLES

FIG. 1*a* (SEQ ID NO: 1) is the amino acid sequence of BSAS

FIG. 1*b* (SEQ ID NO: 2) is the amino acid sequence of SCRAPAS

FIG. 1*c* (SEQ ID NO: 3) is the amino acid sequence of CJAS

FIG. 1*d* (SEQ ID NO: 4) is the amino sequence of MOPAS

FIG. 1*e* (SEQ ID;NO 5) is the amino acid sequence of HAMPAS

FIG. 2*a-c* shows the sequence of antigenic epitopes in BSAS; SCRAPAS and CJAS respectively (SEQ ID NOs: 6-8)

FIG. 2*d* SCRAPAS epitope appears in BSAS (13 of 14 amino acid residues in BSAS and 9 of 14 residues in CJAS (SEQ ID NO: 9);

FIG. 2*e* part of BSAS epitope appears in SCRAPAS and CJAS (SEQ ID NO: 10)

Figure 3B:
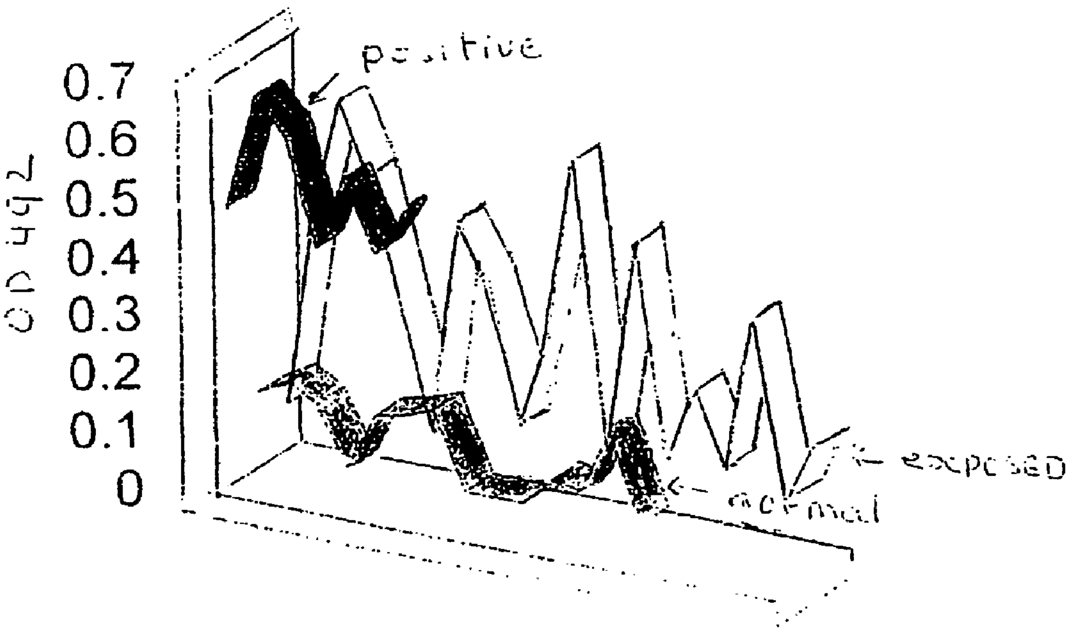
Figure 3C:
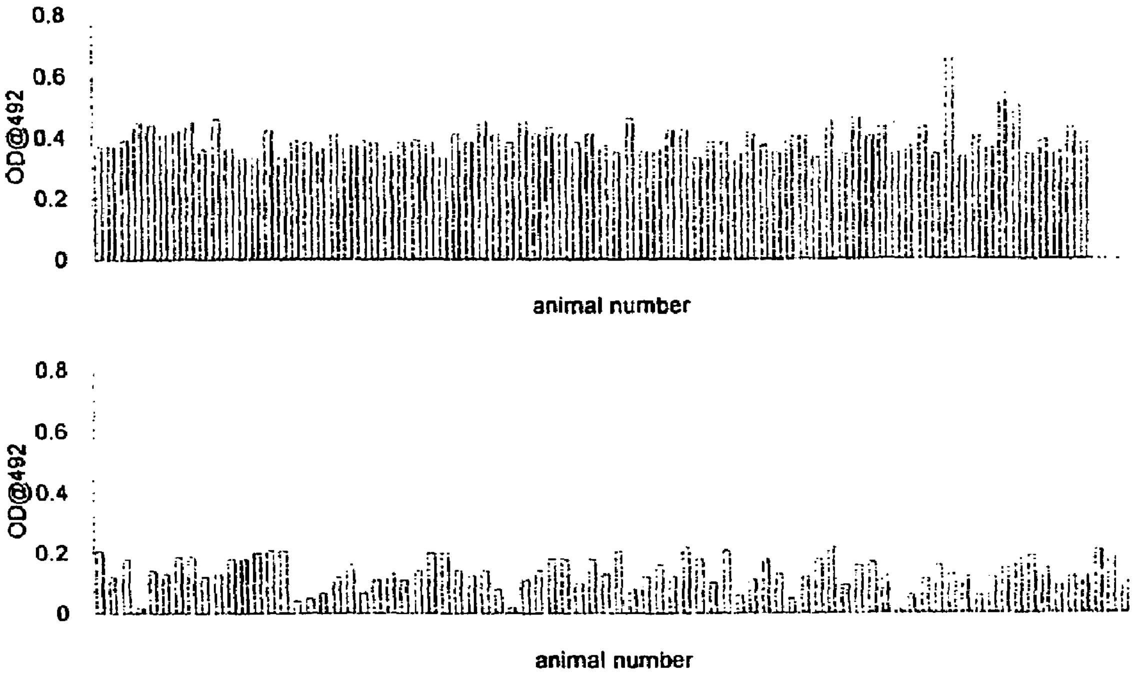

FIG. 3*a* ELISA detection of endogenous anti-BSAS IgG in serum of BSE positive and negative cattle FIG. 3*b* ELISA detection of endogenous anti-BSAS IgG in serum of BSE positive, BSE negative and clinically negative cows from herds which had cases of BSE FIG. 3*c* ELISA detection of endogenous anti-SCRAPAS IgG in serum from scrapie positive and scrapie negative sheep.

Figure 3D:
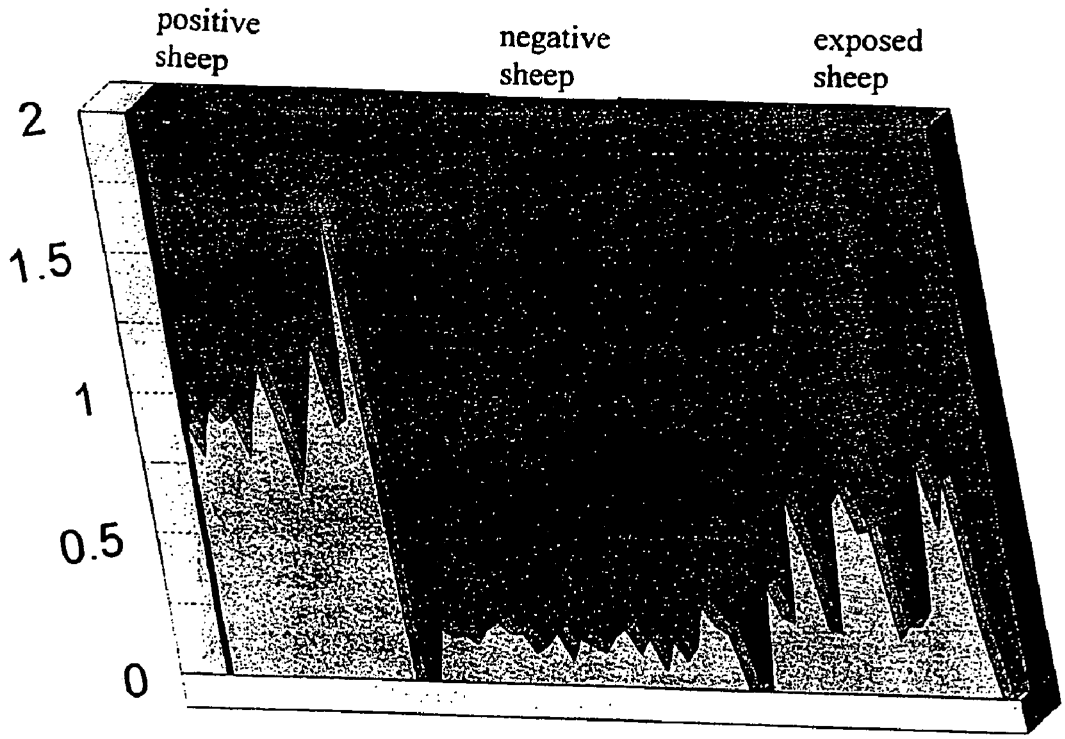
Figure 3E:
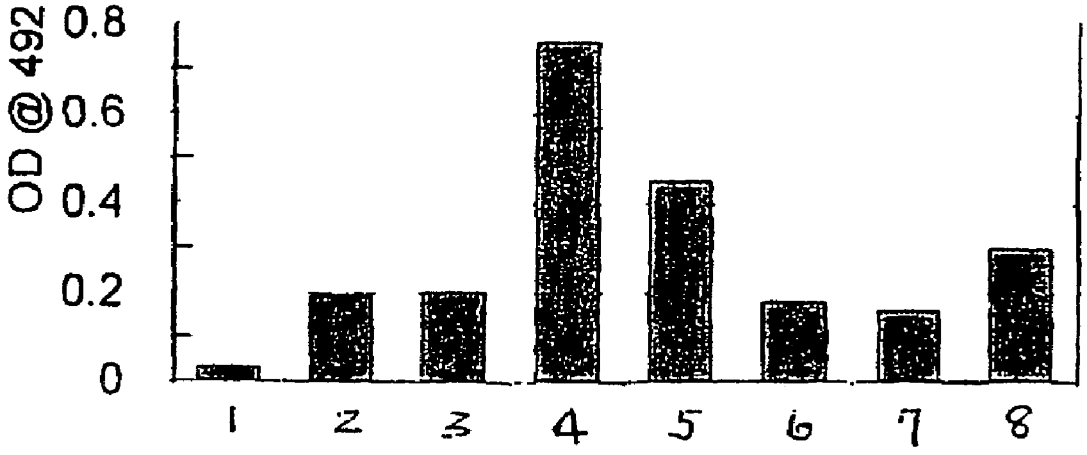
Figure 3F:
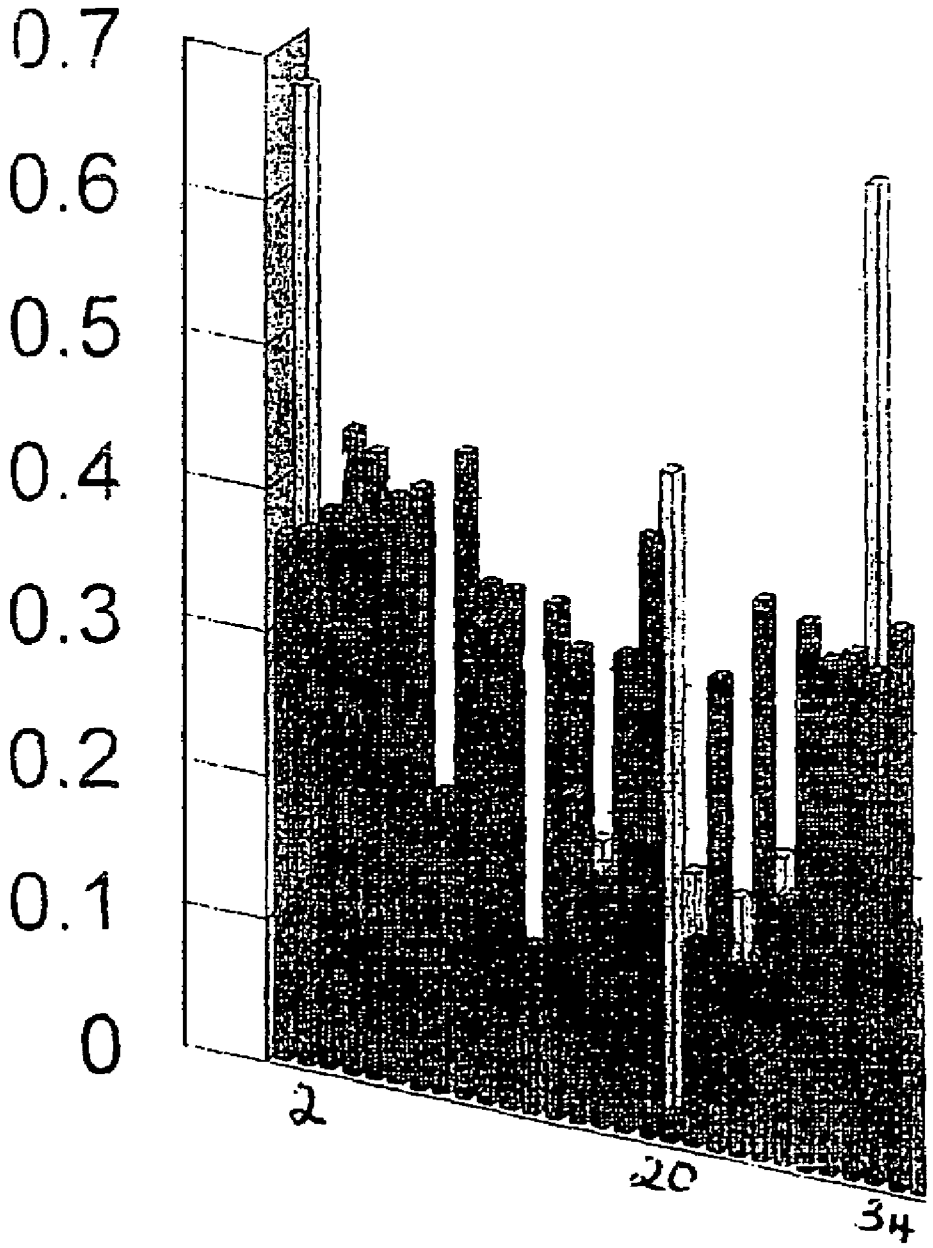

FIG. 3*d* ELISA detection of endogenous anti-SCRAPAS IgG in serum of scrapie positive, scrapie negative sheep and of clinically negative sheep that were exposed to scrapie FIG. 3*e* ELISA detection of CJAS protein in serum of patients with CJD and patients with other neurological diseases FIG. 3*f* ELISA detection of anti-CJAS endogenous IgG in serum of CJD patients and patients with a variety of other neurological diseases.

FIG. 4 sequences of the DNA binding domains of BSAS and SCRAPAS (SEQ ID NO: 11 and 12), (the sequences are 100% homologous) and the sequence of the membrane spanning alpha helix of CJAS (SEQ ID NO. 13)

FIG. 5*a*. evolutionary structural relationship between BSAS, SCRAPAS, CJAS, HAMPAS and MOPAS suggested from cluster analysis of prions and prionins.

Figure 5B:
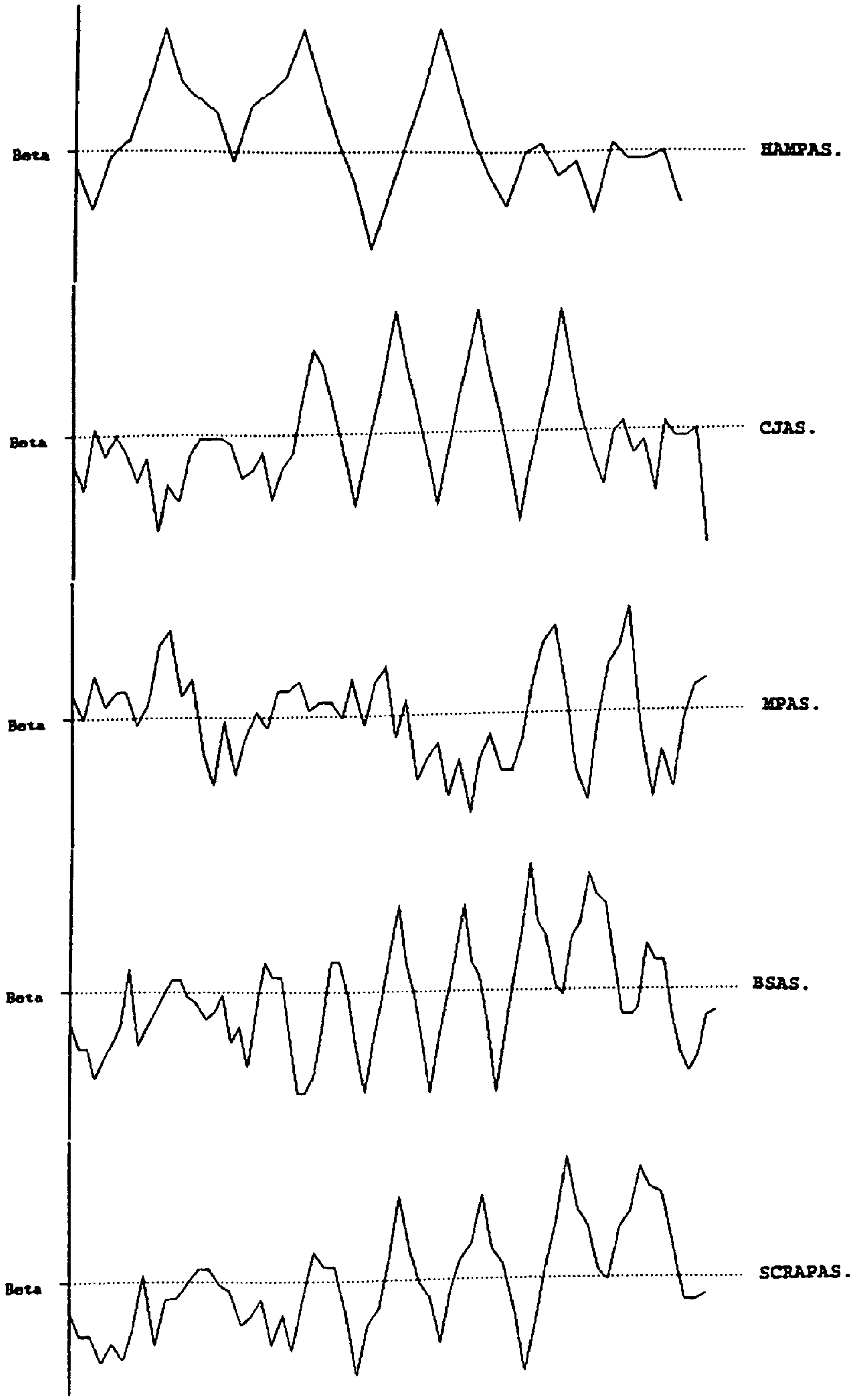

FIG. 5*b* the β-sheet structured characteristics of prionins.

Table 1

Antigen trap ELISA test results from blood and urine of cows and sheep with BSE and scrapie.

BSE dia=clinical diagnosis of animals cv=EC country herd neg=no visible clinical symptoms of BSE but exposed to herds with BSE/scrapie pos=clinical symptoms of BSE/scrapie nz=test material obtained directly Scrapie/BSE free country can 43-83=plasma from "40" Canadian cows which were never exposed to BSE*=all samples tested negative in the ELISA.

Table 2.1 & 2.2

Antibody trap ELISA test results from serum obtain from scrapie positive sheep and serum obtained from scrapie negative sheep from a flock never exposed to scrapie.

Table 3

Antibody trap ELISA test results from serum obtained from BSE positive cows and from BSE negative cows that were never exposed to BSE.

Legend to Figures

FIG. #1*a-e*

The amino acid sequence of the prionins, BSAS, SCRAPAS, CJAS MOPAS and HAMPAS deduced from the mRNA sequence.

FIG. 2

Sequence of antigenic epitopes used to prepare polyclonal antibodies. epitopes were chemically synthesized using solid state technology, purified by HPLC and coupled to key hole limpet haemocyanin. IgG was purified from immune sera and affinity purified on columns of epitope coupled to CN-sepharose.

FIG. 3

(a) Detection of endogenous anti-BSAS IgG in BSE positive cows but not in well-characterised BSE negative cows (plates coated with BSAS and bound antibody detected with anti bovine IgG HRP.

(b) Detection of endogenous anti-BSAS IgG in serum taken from, cows with clinical BSE, clinically normal cows from a herd with cases of BSE and clinically negative cows not exposed to BSE.

(c) Detection of endogenous anti-SCRAPAS IgG in serum taken from scrapie positive sheep but not in serum taken from sheep that were never exposed to scrapie (plates coated with BSAS and anti-SCRAPAS was detected with anti-sheep IgG HRP).

(d) Detection of endogenous anti-SCRAPAS IgG in serum from sheep with clinical scrapie, serum from clinically normal sheep from a flock with several cases of scrapie and serum from sheep never exposed to scrapie.

(e) Detection of CJAS in serum taken from two CJD victims but not in a normal human or in patients with other neurological conditions (plates were coated with anti-SCRAPAS IgG and CJAS was detected with anti-CJAS IgG HRP, (1=physiological aging, 2=diffuse Lewy bodies, 3=Parkinsons, 4=CJD, 5=CJD and Alzheimer's disease, 6=Epilepsy, 7=mixed type dementia, 8=AD.

(f) Detection of endogenous anti-CJAS IgG in serum from two CJD patients but not in serum from 33 clinically normal humans and humans with a variety of neurodegenerative conditions (CJAS epitope was bound to the elisa wells and bound endogenous anti-CJAS IgG was detected with anti human Fc specific IgG HRP) 2 & 34=CJD, 20=Alzheimer's disease 1, 3-19, 21-33 & 35=normals and other diseases.

g) The presence of BSAS and BSAS complexed to IgG fragments in serum isolated from BSE positive cow. 50 ml of was electrophoresed on cationic non SDS PAGE and blotted unto nylon membrane the blots were treated with anti BSAS IgG and the presence of BSAS IgG complexed to BSAS was detected with a mouse anti rabbit IgG coupled to a chemiluminescent substrate, following exposure to X-ray film. IgG was identified in the band with the complex in a separate experiment not shown.

FIG. 4 a, sequence of DNA positive regulators of BSAS and b, SCRAPAS and c, the membrane spanning helix of CJAS.

FIG. 5 a) Evolutionary relationship between the prionins, BSAS, SCRAPAS and CJAS MOPAS and HAMPAS; between bovine PrP, sheep PrP, human PrP, mouse PrP and hamster PrP.

b) The β sheet propensity of the prionins.

Physiological Role of BSAS, SCRAPAS and CJAS in the Neuropathology of BSE, SCRAPIE and CJS.

BSAS, SCRAPAS and CJAS ("prionins") are expressed from within the respective prion genes (as has been shown for the expression of frame shift proteins from within the human APP gene in Alzheimer's disease), structurally, they are closely related; however, the relationship does not appear to be as close as the relationship between the PrPs (see figure) which are not closely related to the prionins (FIG. 5*a*). Prionins are entirely β-sheet derived structures (FIG. 5*b*). In this respect they resemble snake and scorpion toxins and some insect definsins (pore forming proteins) which are predominantly β-sheet structures (Bontems, F. et al., Science 254: 1521-1523 (1991)), but differ from these proteins because they lack cysteine residues; however prionins contain ~20 Trp residues which suggest that they are soluble in cell membranes and other cellular lipid containing structures.

Furthermore, in prionins β-sheets are separated at regular intervals by β turns, and, except for very short sequences at c-terminal and n-terminal ends, the proteins are totally hydrophobic molecules; these structural characteristics are similar to functional domains of another family of proteins which interacts with and alters the secondary structure of other proteins (see PZD and PTB domains Zhou H, et al Nature Struct. Biol. 3:388-393 (1996)).

Structural characteristics mentioned above which indicate that prionins resemble families of pathogenic membrane seeking proteins suggest that prionins are pathogenic proteins. This is supported by the disease specific expression of BSAS, SCRAPAS and CJAS.

Pore forming proteins destroy cells by boring holes in the membranes (Peitsch. M. et al., Mol. Immunol. 27 589-602 (1990)). In the cell cytoplasm they usually aggregate to become soluble. Although neither BSAS nor SCRAPAS contain a "computer defined" transmembrane signal, because they are, highly hydrophobic molecules, they might mimic pore forming proteins by entering plasma membranes using a hydrophobic wedge (see Hill, H. P. et al., Science 251:1481-1485 (1991)) made up mainly of Trp residues). Furthermore extremely high concentration of tryptophan residues in prionins indicate that they may be lipid soluble.

Current dogma holds that PrPs become infectious PrPscs when the secondary structure of the PrP "flips" from predominantly alpha helix to β pleats, and this molecular transformation causes the prions to leave the neuronal membrane and accumulate in extra neuronal spaces (Darcel, C. Vet.Res. Commun. 19:231-252 (1995)). As indicated above, the prionin proteins, can potentially bind to other proteins and enforce the β-plate configuration on the proteins they bind to. Like pore boring proteins prionins can also use the interacting protein as a chaperon for transport in the soluble form to membrane surfaces. PrPs are expressed in lymphoreticular system and are transported to the brain. Like prions, prionins are found in all TSE diseases. Furthermore, the evolutionary relationship to prions (expressed from the same DNA sequences) and the propensity for binding between different proteins which are expressed from the same DNA sequences (see also Baranyi L. et al., Nature Medicine 1:894-901 (1995)), suggest that prionins may be specific molecule that converts PrPC to PrPSC.

Expression of Prionin Proteins.

As stated earlier, certain observations suggest that BSE is caused when cows are inadvertently fed the remains of scrapie infected sheep, and that BSE is transmitted to humans who eat infected meat and this infection produces a disease phenotype which closely resembles CJS. The current invention appears to support this hypothesis, because these three diseases are associated with three species specific unique proteins, which potentially can interact with any other PrP, and therefore, can "infect" any cell they might enter.

BSAS SEQ ID: 1, SCRAPAS SEQ ID NO: 2 and CJAS SEQ ID NO: 3 are expressed specifically in cows infected with BSE, sheep infected with scrapie and humans affected with CJS; all three orf's open from identical translation initiation sequences. BSAS and SCRAPAS are positive DNA binding proteins that can activate a number of genes and can infect across species. The latter two proteins are expressed from alternate reading frames within the major prion genes. Hence if cows ingest SCRAPAS in fodder prepared from sheep with scrapie, SCRAPAS might spuriously bind to a PrP in the lymphoid cells located in the stomach, get transported to the brain, activate translation of BSAS which converts more prions to the pathogenic form and hence initiate BSE in these animals. BSAS entering humans by way of the food chain might activate translation (or transcription) of CJAS, which has the same translation initiation sequence as BSAS and SCRAPAS, and initiate the symptoms of CJS.

From the above discussions it should be obvious that prionins can bypass the blood brain barrier. Once in the brain they might interact with neuronal membrane binding sites usually occupied by PrP. Furthermore since prionins are lipid soluble molecules they can penetrate the plasma membrane, diffuse through lipid layers and enter neurons.

Using BSAS as the example, we believe that this might work as follows:

The PrP protein in neuronal plasma membrane is a target either specific or opportunistic for prionins. BSAS endogenously expressed in, or entering a cell by an external route, interacts with PrPs. On binding to the PrP the rigid, β-sheet structure of BSAS forces the flexible conformation of the PrP to change in a manner which accommodates the BSAS β-sheet structure. This results in the formation of a prion (see Harrison. S. C., Cell 86:343-344 (1996). The soluble BSAS-Prion complex traverses the cytoplasm and leaves the cell through the membrane, enters the lymph vesicular transport system in which it transverses the blood brain barrier and arrives at the surface of a specific subpopulation of neurons. The latter are the usual targets of PrPs. On contact with a neuron BSAS releases from the prion and penetrates the neuronal membrane. The prion cannot enter the membrane in the converted state and is left in the intraneuronal spaces where aggregation occurs with other discarded prions. Alternatively, on release from BSAS the PrP flips back into the original alpha helical PrP state. The cycle of events is amplified as BSAS that enters the neuron overactivates the expression of PrPs.

Since BSAS and SCRAPAS contain the identical positive DNA regulatory sequence FIG. 4, they are likely to activate similar genes and probably autoactivate their own transcription or translation.

Alternatively, prionins can be expressed from a promoter system located 3' downstream, which is believed to program expression of PrP. Whereas PrPs are expressed in appropriate cells throughout life and appear to be normal essential components of neurons, all be it, with functions presently unknown, (but see Schmerling et al., Cell 93:203-214 (1998)). Prionins are probably expressed, secreted and targeted (specific receptors or opportunistic) to neuronal and other non-neuronal cells only in diseased animals.

Support for the notion that prionins are pathogenic was provided by the finding that prionins are bound to a variety of immunoglobulin molecules in the blood of all animals that are clinically positive for BSE/scrapie and humans with clinical CJD. The antibody was also found in a significant number of clinically negative animals that were exposed to BSE or scrapie. The endogenous antibody was never found in animals that were not exposed to BSE/scrapie nor in clinically normal humans that were not exposed to CJD. This indicates that the subject's immune system considered prionins foreign and tried to neutralize them when they were expressed in animals and humans. The immune response to prionins may be extremely important in the control of TSE diseases especially in controlling cross infections. It is also important in detecting latency and of course in presymptomatic diagnosis of TSE diseases. Furthermore it appears likely that prionin expression can be initiated when the appropriate cells, are exposed to some environmental toxin (e.g., microbial or viral infection, intracellular metabolic toxic by products or stress). Such infections might have the effect of first stressing the subject's immune system in a way that it is unable to cope efficiently with other task and secondly the infecting agent may also activate the expression of prionins. This renders the immune system less effective and permits prionins to escape and enter cells where they interact with PrPs.

In summary, prionins acting as pore forming proteins or acting while bound to the prion in the neurons disrupts the lipid layer and enter neurons where they activate expression of a number of genes including PrP and prionins. Prionin molecules remaining on or within the membrane elicit a response from the neuronal immune system. This immune response targets cells containing the prionin molecules and hence selectively destroys these prionin-bearing cells, which takes on the character of an autoimmune reaction against endogenous neurons. Because this autoimmune action selectively targets cells bearing prionins on the surface surrounding cells are for the most part left untouched and the result is the vacoulated spongiform appearance of TSE brains.

The Uses of the Molecules of the Present Invention

A. Diagnostic Uses

Since BSAS, SEQ ID NO: 1; SCRAPAS SEQ ID NO: 2 and CJAS SEQ ID NO: 3, are not expressed at a detectable level by normal animals or humans, the detection of these molecules in a tissue or fluid sample (such as a biopsy sample, or of blood or urine or saliva) is indicative of the presence of the disease in that subject even before any clinical symptoms are present. In Example # 6, the results of 103, mixed, blinded samples including blood, serum and urine were tested using the ELISA test outlined in FIG. 3*a*. All samples from clinically positive samples tested positive for BSAS or SCRAPAS, all clinically normal animals that were never exposed to BSE or scrapie tested negative for BSAS or SCRAPAS whereas up to 30% of the clinically negative animals that were exposed to BSE tested positive. The latter animals were presymptomatic for the disease.

We have used a sensitive sandwich ELISA approaches for detecting BSAS, SCRAPAS and CJAS in cow, sheep and human material and for detecting latency and cross contaminations in animals, foods and blood products; however, the detection of these molecules may be done by any of a variety of immunological methods; a large number of suitable immunoassay formats have been described (Yolken, R. H., Rev. Infect. Dis. 4:35 (1982); Collins, W. P., In: Alternative Immunoassays, John Wiley & Sons, NY (1985); Ngo, T. T. et al., In: Enzyme Mediated Immunoassay, Plenum Press, NY (1985); incorporated by reference herein.

Example: The antibody prepared against the epitope in hamster prionin HAMPAS, SEQ ID NO: 5, can be used to detect CJAS. In lieu of such antibodies, equivalent binding molecules, such as antibody fragments (F(ab'), F(ab')2, single chain antibodies, etc.), recombinant antibodies, chimeric antibodies, etc. may be employed.

As indicated above, immunoassay formats may employ labelled antibodies to facilitate detection. Radioisotopic immunoassays ("RIAs") have the advantages of simplicity, sensitivity, and ease of use. Radioactive labels are of relatively small atomic dimension, and do not normally affect reaction kinetics. Such assays suffer, however, from the disadvantages that, due to radioisotopic decay, the reagents have a short shelf life, require special handling and disposal, and entail the use of complex and expensive analytical equipment. RIAs are described in Laboratory Techniques and Biochemistry in Molecular Biology, by Work, T. S., et al., North Holland Publishing Company, NY (1978), with particular reference to the chapter entitled "An Introduction to Radioimmune Assay and Related Techniques" by Chard, T., incorporated by reference herein.

No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Examples of suitable enzymes, which can be used, include peroxidase, acetylcholine esterase, alpha-glycerol phosphate dehydrogenase, alkaline phosphatase, asparaginase, b-galactosidase, catalase, among many others. Peroxidase and urease are among the more preferred enzyme labels, particularly because of chromogenic pH indicators, which make its activity readily visible to the naked eye.

B. Therapeutic Uses

Significantly, the present invention provides means for treating BSE, scrapie and CJS. Such treatment may be either "prophylactic" or "therapeutic." A prophylactic treatment is one that is provided in advance of any clinical symptom of BSE, scrapie or CJS in order to prevent or attenuate any subsequent onset of the disease. A therapeutic treatment is one that is provided in response to the onset of a symptom of BSE, scrapie or CJS and serves to attenuate an actual symptom of the disease.

In one embodiment, such treatment is provided by administering to an animal or human in need of such treatment an effective amount of an antibody, or an antibody fragment (F(ab'), F(ab')2, single chain antibodies, etc.) or a combination of the above that is capable of binding to BSAS, SCRAPAS or CJAS. As used herein, an effective amount is an amount sufficient to mediate a clinically significant change in the severity of a symptom, or a clinically significant delay in the onset of a symptom.

As will be appreciated, for acute administration, monospecific polyclonal or monoclonal antibodies (or fragments of either) may be administered. More preferably, and especially for chronic administration, the use of non-immunogenic antibodies is preferred. Such molecules can be pseudo-homologous (i.e. produced by any species, but altered to a form that is immunologically indistinct from human antibodies). Examples of such pseudo-homologous molecules include "humanized" (i.e. non-immunogenic in a human) prepared by recombinant or other technology. Such antibodies are the equivalents of the monoclonal and polyclonal antibodies, but are less immunogenic, and are better tolerated by the patient.

Humanized anti CJAS can be produced, for example by replacing an immunogenic portion of each antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041-1043 (1988); Liu, A. Y. et al., Proc. Natl. Acad. Sci. USA 84:3439-3443 (1987); Liu, A. Y. et al., J. Inmunol. 139:3521-3526 (1987); Sun, L. K. et al., Proc. Natl. Acad. Sci. USA 84:214-218 (1987); Nishimura, Y. et al., Canc. Res. 47:999-1005 (1987); Wood, C. R. et al., Nature 314:446-449 (1985)); Shaw et al., J. Natl.Cancer Inst. 80:1553-1559 (1988); all of which references are incorporated herein by reference). General reviews of "humanized" chimeric antibodies are provided by Morrison, S. L. (Science, 229:1202-1207 (1985)) and by Oi, V. T. et al., BioTechniques 4:214 (1986); which references are incorporated herein by reference. Suitable "humanized" antibodies can alternatively be produced by CDR or CEA substitution (Jones, P. T. et al., Nature 321:552-525 (1986); Verhoeyan et al., Science 239:1534 (1988); Beidler, C. B. et al., J. Immunol. 141:4053-4060 (1988); all of which references are incorporated herein by reference).

C. Administration of the Molecules of the Present Invention

Additional pharmaceutical methods may be employed to control the duration of action. Control release preparations may be achieved through the use of polymers to complex or absorb the agents. The controlled delivery may be exercised by selecting appropriate macromolecules (for example polyesters, polyamino acids, polyvinyl pyrrolidone, ethylenevinylacetate, methylcellulose, carboxymethylcellulose, or protamine, sulphate) and the concentration of macromolecules as well as the methods of incorporation in order to control release.

Having now generally described the invention, through references and examples that makes it more readily understood by any one sufficiently skilled in the art, it must be pointed out that these are not intended to be limiting of the present invention, unless specified.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains,and as may be applied to the essential features herein before set forth and as follows in the scope of the claims.

TABLE 1

| sample | source | tissue | BSE dia. | scrapie dia. | ELISA |
|---|---|---|---|---|---|
| 1 | cv | serum | neg | na | – |
| 2 | cv | serum | neg | na | + |
| 3 | cv | serum | pos | na | + |
| 4 | cv | serum | neg | na | – |
| 5 | cv | serum | pos | na | + |
| 6 | cv | serum | pos | na | + |
| 7 | cv | serum | pos | na | + |
| 8 | cv | serum | neg | na | + |
| 9 | cv | serum | neg | na | – |
| 10 | cv | serum | pos | na | + |
| 11 | cv | serum | pos | na | + |
| 12 | cv | serum | neg | na | – |
| 13 | cv | serum | pos | na | + |
| 14 | cv | serum | neg | na | – |
| 15 | cv | serum | neg | na | + |
| 16 | cv | serum | neg | na | – |
| 17 | cv | serum | neg | na | + |
| 18 | cv | serum | pos | na | + |
| 19 | cv | serum | neg | na | – |
| 20 | cv | serum | pos | na | + |
| 21 | cv | serum | neg | na | + |
| 22 | cv | serum | neg | na | – |
| 23 | cv | serum | neg | na | – |
| 24 | cv | serum | neg | na | – |
| 25 | cv | serum | neg | na | – |
| 26 | cv | serum | pos | na | + |
| 27 | cv | serum | pos | na | + |
| 28 | cv | serum | pos | na | + |
| 29 | cv | serum | pos | na | + |
| 30 | cv | serum | pos | na | + |
| 31 | cv | urine | pos | na | + |
| 32 | cv | urine | pos | na | + |
| 33 | cv | urine | pos | na | + |
| 34 | cv | urine | pos | na | + |
| 35 | cv | urine | pos | na | + |
| 36 | cv | urine | neg | na | + |
| 37 | cv | urine | neg | na | + |
| 38 | nz | urine | neg | na | – |
| 39 | nz | urine | neg | na | – |
| 40 | nz | urine | neg | na | – |
| 41 | nz | urine | neg | na | – |
| 42 | nz | urine | neg | na | – |
| 43-83 | can | plasma | all neg | na | – * |
| 84 | cv | plasma | na | neg | – |
| 85 | cv | plasma | na | neg | – |
| 86 | cv | plasma | na | neg | – |
| 87 | cv | plasma | na | pos | + |
| 88 | cv | plasma | na | neg | – |
| 89 | cv | plasma | na | pos | + |
| 90 | cv | plasma | na | neg | – |
| 91 | cv | plasma | na | pos | + |
| 92 | cv | plasma | na | pos | + |
| 93 | cv | plasma | na | neg | – |
| 94 | cv | plasma | na | neg | – |
| 95 | cv | plasma | na | pos | + |
| 96 | cv | plasma | na | pos | + |
| 97 | cv | plasma | na | pos | + |
| 98 | cv | plasma | na | neg | – |
| 99 | cv | plasma | na | neg | – |
| 100 | cv | plasma | na | pos | + |
| 101 | cv | plasma | na | neg | – |
| 102 | cv | plasma | na | pos | + |
| 103 | cv | plasma | na | pos | + |

TABLE 2-1

| mean absorbance | status | mean absorbance | status |
|---|---|---|---|
| 367 | POS | 211 | NEG |
| 373 | POS | 117 | NEG |
| 389 | POS | 182 | NEG |
| 449 | POS | 19 | NEG |
| 437 | POS | 143 | NEG |
| 409 | POS | 131 | NEG |

TABLE 2-1-continued

| mean absorbance | status | mean absorbance | status |
|---|---|---|---|
| 419 | POS | 189 | NEG |
| 450 | POS | 189 | NEG |
| 362 | POS | 122 | NEG |
| 362 | POS | 127 | NEG |
| 360 | POS | 172 | NEG |
| 331 | POS | 183 | NEG |
| 333 | POS | 204 | NEG |
| 419 | POS | 206 | NEG |
| 331 | POS | 206 | NEG |
| 392 | POS | 40 | NEG |
| 383 | POS | 51 | NEG |
| 360 | POS | 73 | NEG |
| 368 | POS | 117 | NEG |
| 357 | POS | 152 | NEG |
| 391 | POS | 78 | NEG |
| 383 | POS | 111 | NEG |
| 347 | POS | 128 | NEG |
| 378 | POS | 112 | NEG |
| 394 | POS | 138 | NEG |
| 387 | POS | 199 | NEG |
| 333 | POS | 202 | NEG |
| 410 | POS | 147 | NEG |
| 379 | POS | 122 | NEG |
| 453 | POS | 137 | NEG |
| 413 | POS | 80 | NEG |
| 431 | POS | 16 | NEG |
| 414 | POS | 108 | NEG |
| 376 | POS | 139 | NEG |
| 412 | POS | 181 | NEG |
| 366 | POS | 184 | NEG |
| 348 | POS | 10 | NEG |
| 463 | POS | 181 | NEG |
| 350 | POS | 134 | NEG |
| 362 | POS | 213 | NEG |
| 416 | POS | 83 | NEG |
| 417 | POS | 115 | NEG |
| 334 | POS | 164 | NEG |
| 380 | POS | 123 | NEG |
| 380 | POS | 217 | NEG |
| 346 | POS | 177 | NEG |
| 418 | POS | 103 | NEG |
| 373 | POS | 208 | NEG |
| 349 | POS | 65 | NEG |

TABLE 2-2

| | | | |
|---|---|---|---|
| 399 | POS | 115 | NEG |
| 401 | POS | 167 | NEG |
| 331 | POS | 129 | NEG |
| 448 | POS | 48 | NEG |
| 341 | POS | 123 | NEG |
| 473 | POS | 179 | NEG |
| 397 | POS | 223 | NEG |
| 426 | POS | 90 | NEG |
| 352 | POS | 165 | NEG |
| 368 | POS | 167 | NEG |
| 433 | POS | 116 | NEG |
| 342 | POS | 5 | NEG |
| 598 | POS | 58 | NEG |
| 334 | POS | 104 | NEG |
| 397 | POS | 158 | NEG |
| 358 | POS | 129 | NEG |
| 538 | POS | 120 | NEG |
| 512 | POS | 58 | NEG |
| 336 | POS | 118 | NEG |
| 389 | POS | 153 | NEG |
| 349 | POS | 179 | NEG |
| 433 | POS | 188 | NEG |
| 375 | POS | 146 | NEG |
| | | 92 | NEG |
| | | 119 | NEG |
| | | 123 | NEG |
| | | 208 | NEG |

TABLE 2-2-continued

| | | |
|---|---|---|
| | 184 | NEG |
| | 105 | NEG |

TABLE 3

| Mean absorbance | Status |
|---|---|
| 669 | POS |
| 455 | POS |
| 684 | POS |
| 518 | POS |
| 572 | POS |
| 546 | POS |
| 453 | POS |
| 474 | POS |
| 668 | POS |
| 457 | POS |
| 588 | POS |
| 572 | POS |
| 813 | POS |
| 579 | POS |
| 496 | POS |
| 515 | POS |
| 589 | POS |
| 60 | NEG |
| 14 | NEG |
| 44 | NEG |
| 22 | NEG |
| 206 | NEG |
| 22 | NEG |
| 53 | NEG |
| 214 | NEG |
| 31 | NEG |
| 22 | NEG |
| 196 | NEG |
| 98 | NEG |
| 188 | NEG |
| 259 | NEG |
| 39 | NEG |
| 179 | NEG |
| 96 | NEG |
| 169 | NEG |
| 133 | NEG |

TABLE 3-continued

| Mean absorbance | Status |
|---|---|
| 204 | NEG |
| 89 | NEG |
| 152 | NEG |
| 41 | NEG |
| 102 | NEG |
| 30 | NEG |
| 111 | NEG |
| 103 | NEG |
| 105 | NEG |
| 290 | NEG |
| 172 | NEG |
| 131 | NEG |
| 147 | NEG |
| 58 | NEG |
| 118 | NEG |
| 33 | NEG |
| 41 | NEG |
| 268 | NEG |
| 153 | NEG |
| 137 | NEG |
| 101 | NEG |
| 121 | NEG |
| 83 | NEG |
| 74 | NEG |
| 66 | NEG |
| 78 | NEG |
| 200 | NEG |
| 191 | NEG |
| 89 | NEG |
| 120 | NEG |
| 111 | NEG |
| 82 | NEG |
| 187 | NEG |
| 238 | NEG |
| 114 | NEG |
| 41 | NEG |
| 110 | NEG |
| 70 | NEG |
| 239 | NEG |
| 41 | NEG |
| 118 | NEG |

What is claimed is:

1. A protein molecule free of natural contaminants selected from the group consisting of BSAS, SCRAPAS, CJAS, and HAMPAS the sequence of which is SEQ ID NO:1, SEQ ID NO:2, SEQ ID NO:3, and SEQ ID NO:5, respectively.

2. A purified antibody that cross reacts with either BSAS, SCRAPAS, CJAS or HAMPAS, the sequence of which is SEQ ID NO:1, SEQ ID NO:2, SEQ ID NO:3 and SEQ ID NO:5, respectively.

3. The antibody of claim 2, wherein the antibody is produced by immunizing appropriate animals with polypeptide domains of BSAS or SCRAPAS or CJAS or HAMPAS, respectively.

4. The antibody of claim 2 that cross reacts with either BSAS, SCRAPAS or CJAS, wherein said antibody is produced endogenously by a cow or by a sheep or by a human, respectively.

5. The antibody of claim 2, wherein the antibody is an antibody fragment, a single chain antibody, a monospecific polyclonal antibody, a monoclonal antibody, a recombinant antibody or a humanized antibody.

6. A method for the detection of a TSE in humans or animals comprising detecting in a tissue or fluid sample a protein as defined by SEQ ID NO:1, SEQ ID NO:2, or SEQ ID NO:3 or an antibody that cross reacts with any of the proteins as defined by SEQ ID NO:1, SEQ ID NO:2, or SEQ ID NO:3.

7. The method of claim 6 wherein the TSE is bovine spongiform encephalopathy (BSE), scrapie disease or Creutzfeldt-Jakob Syndrome (CJS).

* * * * *